(12) United States Patent
Dick et al.

(10) Patent No.: US 11,540,944 B2
(45) Date of Patent: Jan. 3, 2023

(54) DEVICE AND METHOD FOR VITREOUS HUMOR SURGERY

(71) Applicant: Carl Zeiss Meditec AG, Jena (DE)

(72) Inventors: Manfred Dick, Gefell (DE); Marcus Blum, Erfurt (DE); Matthias Reich, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 965 days.

(21) Appl. No.: 15/433,666

(22) Filed: Feb. 15, 2017

(65) Prior Publication Data

US 2017/0216096 A1    Aug. 3, 2017

Related U.S. Application Data

(62) Division of application No. 13/701,470, filed as application No. PCT/EP2011/002710 on Jun. 1, 2011, now Pat. No. 9,579,153.

(30) Foreign Application Priority Data

Jun. 1, 2010   (DE) .................... 10 2010 022 635.1

(51) Int. Cl.
*A61F 9/008* (2006.01)
*A61F 9/009* (2006.01)
*A61B 18/20* (2006.01)

(52) U.S. Cl.
CPC .......... *A61F 9/00825* (2013.01); *A61B 18/20* (2013.01); *A61F 9/008* (2013.01);
(Continued)

(58) Field of Classification Search
CPC .. A61F 9/00825; A61F 9/00802; A61F 9/008; A61F 9/009; A61F 9/00804;
(Continued)

(56) References Cited

U.S. PATENT DOCUMENTS

| 6,204,955 B1 | 3/2001 | Chao et al. |
| 6,726,679 B1 | 4/2004 | Dick et al. |
| | (Continued) | |

FOREIGN PATENT DOCUMENTS

| DE | 10 202 036 A1 | 7/2003 |
| DE | 103 23 422 A1 | 4/2004 |
| | (Continued) | |

OTHER PUBLICATIONS

Nagy et al., "Initial Clinical Evaluation of an Intraocular Femtosecond Laser in Cataract Surgery," Journal of Refractive Surgery, 25, 1053-1059, 2009.

(Continued)

*Primary Examiner* — John R Downey
*Assistant Examiner* — Sebastian X Lukjan
(74) *Attorney, Agent, or Firm* — DeWitt LLP

(57) ABSTRACT

A device and a method for the femtosecond laser surgery of tissue, especially in the vitreous humor of the eye. The device includes an ultrashort pulse laser with pulse widths in the range of approximately 10 fs-1 ps, especially approximately 300 fs, pulse energies in the range of approximately 5 nJ-5 μJ, especially approximately 1-2 μJ and pulse repetition rates of approximately 10 kHz-10 MHz, especially 500 kHz. The laser system is coupled to a scanner system which allows the spatial variation of the focus in three dimensions (x, y and z). In addition to the therapeutic laser/scanner optical system, the device includes a navigation system.

15 Claims, 3 Drawing Sheets

(52) U.S. Cl.
CPC .......... *A61F 9/009* (2013.01); *A61F 9/00802* (2013.01); *A61F 9/00804* (2013.01); *A61F 9/00821* (2013.01); *A61F 2009/0087* (2013.01); *A61F 2009/00844* (2013.01); *A61F 2009/00851* (2013.01); *A61F 2009/00863* (2013.01); *A61F 2009/00872* (2013.01); *A61F 2009/00874* (2013.01); *A61F 2009/00887* (2013.01)

(58) Field of Classification Search
CPC ........ A61F 9/00872; A61F 2009/00887; A61F 2009/00844; A61F 2009/00851; A61F 2009/00863; A61F 2009/0087; A61F 2009/00874; A61F 9/00821; A61B 18/20
See application file for complete search history.

(56) References Cited

U.S. PATENT DOCUMENTS

| | | | | |
|---|---|---|---|---|
| 6,789,900 | B2* | 9/2004 | Van de Velde | A61F 9/008 351/221 |
| 9,579,153 | B2* | 2/2017 | Dick | A61F 9/008 |
| 10,617,564 | B1* | 4/2020 | Andersen | A61F 9/0079 |
| 2002/0060778 | A1* | 5/2002 | Su | A61F 9/008 351/206 |
| 2004/0039378 | A1* | 2/2004 | Lin | A61B 18/20 606/6 |
| 2005/0165387 | A1 | 7/2005 | Lubatschowski et al. | |
| 2005/0286019 | A1* | 12/2005 | Wiltberger | A61B 3/0091 351/211 |
| 2006/0100677 | A1* | 5/2006 | Blumenkranz | A61F 9/008 607/89 |
| 2006/0106371 | A1* | 5/2006 | Muhlhoff | A61F 9/008 606/5 |
| 2007/0219543 | A1 | 9/2007 | Yee | |
| 2007/0282313 | A1* | 12/2007 | Huang | A61B 3/1005 606/5 |
| 2008/0027519 | A1* | 1/2008 | Guerrero | A61F 9/008 607/89 |
| 2008/0183159 | A1 | 7/2008 | Preuss et al. | |
| 2009/0048586 | A1* | 2/2009 | Krueger | A61F 9/008 606/5 |
| 2009/0143772 | A1* | 6/2009 | Kurtz | A61F 9/008 606/4 |
| 2010/0274232 | A1 | 10/2010 | Bischoff et al. | |
| 2010/0290007 | A1* | 11/2010 | Van de Velde | A61B 3/1025 351/221 |
| 2011/0118609 | A1* | 5/2011 | Goldshleger | A61B 3/0083 600/476 |
| 2011/0245820 | A1* | 10/2011 | Papac | A61B 1/0653 606/15 |
| 2014/0276679 | A1* | 9/2014 | Bor | A61F 9/0084 606/6 |

FOREIGN PATENT DOCUMENTS

| | | |
|---|---|---|
| DE | 10 2007 035 850 A1 | 2/2009 |
| DE | 11 2008 002 380 T5 | 6/2010 |
| EP | 1 212 022 B1 | 6/2002 |
| EP | 1 663 087 | 6/2006 |
| WO | WO 01/13838 A1 | 3/2001 |
| WO | WO 2005/070358 A1 | 8/2005 |
| WO | WO 2008/017428 A2 | 2/2008 |

OTHER PUBLICATIONS

Schmidt, "Macular-threatening tration detachment of the retina in diabetic proliferative retinopathy, treated by laser", International Opthalmology, 21, 99-106, 1997.

Application and File History for U.S. Appl. No. 13/701,470, filed Jan. 15, 2013. Inventors: Manfred Dick et al.

* cited by examiner

DEVICE AND METHOD FOR VITREOUS HUMOR SURGERY

CROSS-REFERENCE TO RELATED APPLICATIONS

This application is a division of application Ser. No. 13/701,470, filed Jan. 15, 2013, entitled "Device and Method for Vitreous Humor Surgery," which in turn is a National Phase entry of PCT Application No. PCT/EP2011/002710, filed Jun. 1, 2011, which claims priority from German Application No. 10 2010 022 635.1, filed Jun. 3, 2010, each of which is hereby fully incorporated herein by reference.

TECHNICAL FIELD

The present invention relates to a device and a method for the femtosecond laser surgery of tissue, especially in the vitreous humor of the eye.

BACKGROUND

It is known that non-linear interactions and, at higher pulse energies or energy densities, a photodisruption in particularly optical materials or tissue can be generated with the help of femtosecond laser radiation.

In everyday clinical life, for example, this is utilized in eye-surgical lasers such as the "Visumax" from Carl Zeiss Meditec AG. Here the laser system is provided with a femtosecond (fs) laser beam source, the pulse energy of which is adjusted beforehand at a predetermined repetition rate (e.g., 500 kHz) of the laser pulses in a relevant range of, e.g., 50 nJ-5 µJ in order to always reliably generate a photodisruption in the tissue. With regard to a treatment of the cornea of the eye, a minimal focal diameter in the 1 µm range can be achieved with a comparatively large numerical aperture of the focusing optics (approximately 0.3).

Optimal parameters have become known for the fs laser therapy of the crystalline lens which ensure quick treatment and minor collateral damages (EP 1212022 B1). With apertures of approximately 0.2, focal diameters of approximately 5 µm can be achieved. Such an arrangement is also known from EP 1663087 or from the applicant's WO 2008/017428, the entire content of which is hereby incorporated by reference.

For the treatment of the eye fundus or the retina, only coagulation lasers (e.g., frequency-doubled Nd:YAG with a wavelength of 532 nm or also 561 and 659 nm) are known which can coagulate eye tissue, particularly of the retina, and also atrophy bleedings through thermal effects.

With an approximate volume of 80%, the vitreous humor is the largest structure of the eye. It consists of a gelatinous complex of hyaluronic acid, water, and a collagen framework. In the course of life, the vitreous humor undergoes an aging process which causes significant structural changes. Those changes are essentially a type of liquefaction of the vitreous humor which can result in detachments of the vitreous humor from the surrounding layers of the eye, particularly the retina and the capsular bag of the lens, which can entail medical complications.

A frequent serious complication is a retinal detachment which can occur in the periphery of an incomplete vitreous detachment. It is frequently induced by tensile forces of vitreous humor strands which connect the partially detached vitreous humor to the retina.

Such complications are commonly treated with a vitrectomy, wherein the eye is opened up and the vitreous humor surgically removed. However, this surgical procedure causes great stress for the patient, entails high costs due to the necessary hospital treatment and risks during the procedure.

It has been demonstrated in rare cases that traction causing vitreous humor strands can be severed with focused radiation from an Nd:YAG laser, thereby avoiding a vitrectomy [D. Schmidt, "Macular-threatening traction detachment of the retina in a diabetic proliferative retinopathy, treated by laser," International Ophthalmology, 21, 99-106, 1997]. The severing is effected by the pressure wave of photodisruptions which are caused by the high pulse energies in the mJ range at pulse durations of a few ns. Said pressure waves also damage the surrounding tissue, making the use of this method impossible in immediate proximity of the retina. The laser spot is still placed manually by the physician after observation through a slit lamp microscope.

SUMMARY

It is known that precise incisions in transparent media without damage to the surrounding tissue can be made with ultrashort laser pulses. Corresponding devices and methods have thus far only become known in the ophthalmology for the treatment of the anterior eye segment, particularly the cornea and the crystalline lens and are not applicable for vitreous humor surgery due to geometric and applicative constraints.

The problem addressed by the present invention is that of identifying devices and methods for a minimally invasive vitreous humor and retinal surgery.

The features according to the invention are further described in the following paragraphs:

The device, according to the invention, consists of an ultrashort pulse laser with pulse widths in the range of approximately 10 fs-1 ps, especially approximately 300 fs, pulse energies in the range of approximately 5 nJ-5 µJ, especially approximately 1-2 µJ, and pulse repetition rates of approximately 10 kHz-10 MHz, especially 500 kHz. According to the invention, the laser system is coupled to a scanner system which allows the spatial variation of the focus in three dimensions (x, y, and z). In addition, beam guidance by an optical system is provided for imaging the scanner mirrors for the lateral focal spot displacement (x, y) in the immediate proximity of the pupil of the eye to be treated (so-called conjugate plane). The bundle diameter of the laser beam in the eye pupil is preferably between 2 and 4 mm. The beam divergence can be varied in order to realize a shift of the focal position in axial direction (z-scan).

Preferably, the eye to be treated is mechanically coupled via a contact glass which is suctioned to the cornea or the sclera of the eye using a vacuum. In this case, the laser radiation is coupled in the eye via the contact glass.

If a contact glass is used, a focusing optics with a numerical aperture of approximately 0.05-0.2, especially approximately 0.1, is provided.

In addition to the outlined therapeutic laser scanner optical system, the device according to the invention furthermore consists of a navigation system coupled thereto and which comprises, e.g., a confocal optical detection and/or optical coherence tomography (OCT) and/or further optical measurement methods. Examples for further measurement methods are triangulation, fringe projection, fundus cameras and ophthalmological microscopes.

These detection methods provided local information of the therapeutic target regions in the retina or the vitreous humor of the eye.

If a confocal detection is used, a self-calibration of the navigation and therapy data is provided.

With an OCT and/or other optical navigation methods, a calibration procedure is preferably provided in order to synchronize the navigation device and the therapy device.

In one version of the calibration, spots and/or spot lines are preferably placed in the vitreous humor of the eye by the therapy laser which lead to local disruption bubbles and which can subsequently be localized using the navigation system. A calibration algorithm is used for synchronizing the therapy and navigation data. As a result, a locally precise laser surgery in the vitreous humor and/or the retina is possible following the calibration procedure.

According to the invention, the device has a control system which provides control data for the laser radiation and the scanner system.

When said control data are compiled, it is taken into account that in case of incisions in the vitreous humor, the radiation exposure of the retina does not exceed the known thresholds for damage. For this purpose, the energy and power density are calculated locally on the retina using an optical model, and the temporal and spatial sequence of the applied pulses is varied during the incision phase until the radiation exposure for every location on the retina is below the damage threshold.

With progressing liquefaction and the associated increasing detachment of the vitreous humor with advancing age, medical problems can occur when vitreous humor strands apply tensile loads on small segments of the retina. A complete liquefaction no longer poses this threat. Therefore, the objective of the methods and devices of this invention is that of inducing and fostering liquefaction of the vitreous humor. According to the invention, this is achieved with incisions or perforations with the ultrashort pulse laser radiation, which sever vitreous humor strands and thus increase the metabolic exchange. Examples for incision geometries according to the invention are shown in FIGS. 2a and 2b. They resemble plane incisions, which are essentially aligned vertically to the optical axis of the eye, or to a structure that resembles onion layers. It is advantageous to distribute the incisions relatively evenly in the volume of the vitreous humor, wherein a safety distance to the retina must be observed. According to the invention, the device therefore contains a navigation means which detects at least the posterior boundary layers of the crystalline lens and the retina.

In case of already existing tensile loads on the retina due to partial vitreous detachments, the invention provides for the identification of the vitreous body strand structures which cause said tensile loads and the reduction of the tensile forces using appropriate relief incisions.

The strand structures of the vitreous humor have certain points in the eye to which they adhere particularly strongly. Said points are Wieger's ligament at the periphery of the posterior lens capsule, Salzmann's vitreous base in the region of the ora serrata, and Martegiani's ring near the papilla. These regions frequently are the points of origin of the tension loads. Therefore, a further objective of the methods and devices described in this invention is to provide minimally invasive relief incisions in the region of these three zones. Corresponding incision geometries according to the invention are shown by way of example in FIG. 4. The depicted three incisions can be carried out individually or in combination with one another.

For the incision in the area of Salzmann's vitreous base, a contact glass with integrated deflection mirrors (a so-called mirror contact glass) can preferably be used in order to focus the laser radiation in the extreme periphery of the eye. According to the invention, an adaptive mirror system can also be introduced in the beam path for compensating the wavefront distortions which occur during focusing of the laser radiation in the eye at the required acute angle of incidence and thus increasing the incision quality.

According to the invention, with an incision near Wieger's ligament, an anterior vitreous detachment can be induced. For example, this can be sensible in conjunction with cataract surgery and reduces the rate of retinal detachments. Such a vitreous humor incision is particularly preferred in conjunction with other laser incisions in the course of a surgical therapy of a cataract and can be executed with the same device. The other incisions are, e.g., a capsulorrhexis and a segmentation of the cataract as described (inter alia) by Z. Nagy [Z. Nagy et al., "Initial Clinical Evaluation of an Intraocular Femtosecond Laser in Cataract Surgery," Journal of Refractive Surgery, 25, 1053-1059, 2009]. Therefore, the appropriate device consists of a navigation device for the region of the crystalline lens, which is preferably based on the principle of confocal detection.

FIG. 5 depicts an example of a heavily localized retinal detachment which is caused by the tensile effect of strands during the vitreous detachment. For such a clinical picture, the invention provides for the severing of the appropriate strand along the indicated, greatly limited incision geometry. For the localization of such structures, an OCT measuring system is preferably integrated in the laser device. Particularly, the OCT measuring beam is preferably coaxially superimposed with the beam axis of the processing laser and the area to be treated is scanned immediately before the therapy incision.

Floaters (also called mouches volantes) are generally benign inhomogeneities in the vitreous humor but which are sometimes perceived as very irritating by the affected person. Floaters are rarely treated because they can only be removed with invasive procedures (vitrectomy). According to the invention, larger inhomogeneities can be detected spatially resolved with a suitable measurement method, e.g., OCT, and selectively reduced to smaller pieces or resolved through the application of laser disruptions.

For the described laser-surgical applications in the vitreous humor, the laser emission is preferably kept in the near infrared spectral range, particularly preferred between 800 nm and 1100 nm.

Cystoid macular edema is a disorder which occurs in the area of the retina and treatment is currently difficult. Fluid accumulates in the area of the macula and impairs vision. With the device according to the invention, a minimally invasive therapy is possible by generating a thin channel from the vitreous humor into the cyst with focused fs laser radiation (FIG. 6). This allows for the fluid to flow into the vitreous chamber and the subsequent reduction of the swelling. According to the invention, an integrated navigation system, which is, for example, based on the principle of optical coherence tomography (OCT), is used for visualizing the structure of the edema. Using suitable input devices, the physician defines the geometry of the channel for the puncture which is subsequently carried out with the laser radiation. Advantageously, a coagulating laser as known from ophthalmology can be integrated in the device, and the laser beam of said laser is coaxially superimposed with the fs laser beam. As a result, small bleedings from blood vessels, which are caused by the puncture, can be stopped immediately.

Macular rotation is a further known invasive, retina-surgical method for AMD, in which the macular area of the retina is cut out and rotated in order to position still unimpaired photoreceptors in the optical axis of the eye and improve the patient's vision.

According to the invention, minimally invasive photodisruption incisions are made with the therapy system for severing the edge of the macula after navigation of the macula, e.g., in the OCT image. Following this minimally invasive procedure, the actual macular rotation can be carried out invasively, wherein the overall invasiveness can be greatly reduced.

Different wavelengths of the fs laser radiation are provided for the incision guidance in the retina.

The use of a wavelength in the green spectral range, e.g., 532 nm, which is greatly absorbed in the retinal pigment epithelium (RPE), allows for a particularly good incision in this layer. In a first work step, the RPE can be severed by focusing on said RPE, and then the adjacent transparent retinal nerve tissue can be successively severed due to the photodisruption when the z-scan distance is shortened during a continuous xy-scan.

Stimulation of the retinal pigment epithelium for age-related macular degeneration (AMD) using coagulation lasers or μs lasers for selective retina therapy (SRT) is known. According to the invention, the fs laser system is operated in the yellow spectral range (approximately 560-590 nm) in order to loosen the RPE layer with spots, lines, and structures within the macula and through the macular pigment and thus induce a regeneration of said layer. For example, grid structures with approximately 10-50 μm laser spots and distances of 200-500 μm are provided.

The invention can also be summarized as follows:

Device and method for 3D scanner-guided focusing of fs laser radiation, wherein a calibration of an OCT system using test spots in front of the retina, which are introduced by an fs laser, is used to execute layer-resolved laser surgery in the retina.

Alternatively, the invention is characterized by a device for surgical manipulation of the posterior eye segment with ultrashort laser radiation, wherein the device has an imaging optical system and a scanner system which allows for the positioning of the focus of the laser radiation in three dimensions in the posterior eye segment, wherein the device has an optical beam guidance system which images the scanner mirror(s), which cause(s) a lateral shift of the focal position, near the eye pupil, and the eye is coupled to the device with a contact glass via a vacuum suction system.

A further aspect of the invention is a device for surgical manipulation of the posterior eye segment with ultrashort laser radiation, wherein the device has an imaging optical system and the ultrashort laser radiation is superimposed with a second laser radiation with coagulating effect.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

In the following, the invention is further described with the drawings.

Figure 1:
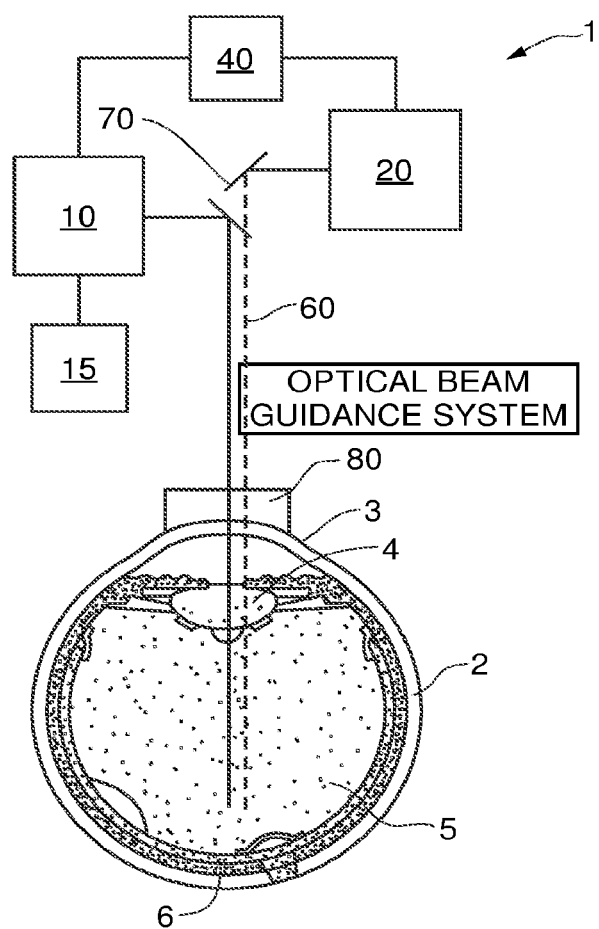
FIG. 1 is a schematic depiction of the device according to the invention.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

FIG. 1 shows a schematic depiction of a treatment device 1 according to the present invention. The treatment device 1 comprises a detection device 10 having an optical confocal and/or optical coherence tomography device in the form of the sensors 15. In addition, a processing laser 20 is provided. The detection device 10 and the processing laser 20 are connected to a control device 40. A corresponding optical path can be directed from the detection device 10 and the processing laser 20 via scanner mirrors into the eye 2. The processing laser 20 is an fs laser with a pulse duration of 300 fs, and the laser beam 60 of said fs laser can be guided three-dimensionally by a deflection unit 70 and thus focused on structures in the eye fundus.

The inner structure of the eye 2 is detected using the detection device 10. The sensors 15 are supporting said detection and determine once again a three-dimensional image of said inner structure. This information is transmitted to the control device 40 which calculates firing coordinates (and thus the spot distances) for the processing laser 20 using, e.g., a finite element model. It is particularly preferred that the data are first transmitted to the control device for calculating preferred incision geometries which approach the desired change of the vitreous humor or the retinal tissue. Once the calculation is concluded, firing parameters are provided for subsequently applying said incision geometries in the eye tissue using the laser. The control device transmits said data to the processing laser 20 which initiates the correspondingly predetermined treatment. This allows for therapeutic incisions which are generated using bubble fields generated by disruptions from an ultrashort pulse laser system used as processing laser 20. In addition, the control device 40 monitors the impinged total energy in order to prevent the permissible dose to be exceeded.

The eye 2 is coupled to the treatment device 1 via a contact glass 80 which is suctioned with a vacuum to the cornea 3 in order to prevent movements of the eye during treatment.

Figure 2:
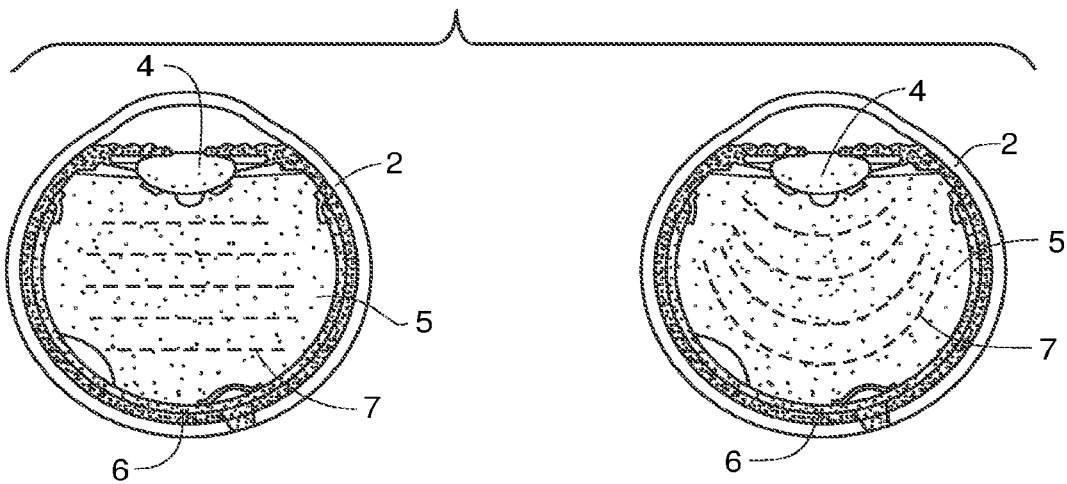
FIG. 2 is a depiction of the vitreous humor with example incision lines.

In addition to the crystalline lens 4, the vitreous humor 5 and the retina 6 are further essential components of the eye 2. The focusing optics (not depicted) for the laser beam 60 has a numerical aperture of 0.1 which, in conjunction with the deflection unit 70, allows for a very precise guidance of the focus of the treatment laser 20 also in the area behind the crystalline lens 40. FIG. 2 depicts different incision geometries 7 within the vitreous humor 5 for the liquefaction of the vitreous humor.

Figure 3:
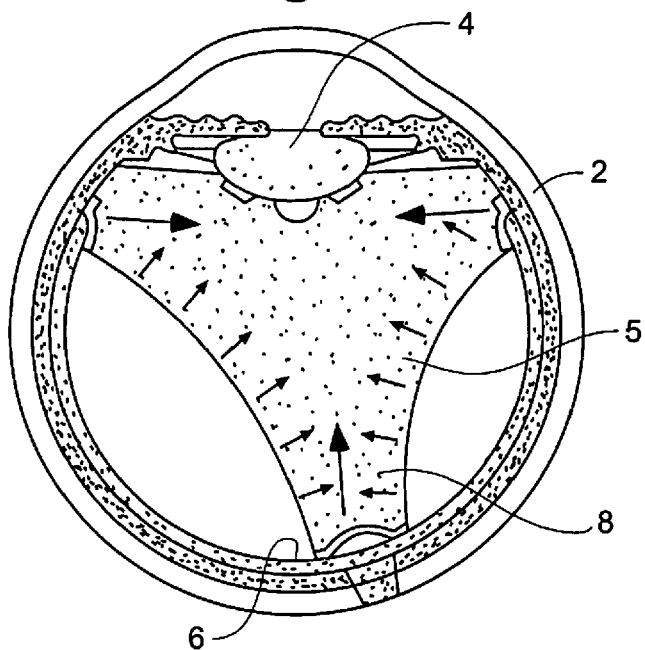
FIG. 3 depicts the effect of a vitreous detachment.
Figure 4:
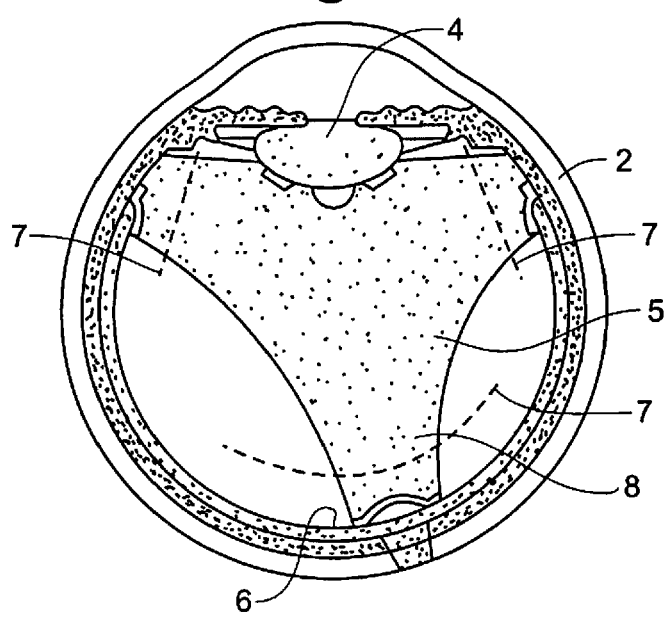
FIG. 4 depicts example incision lines in case of a vitreous detachment.

FIG. 3 depicts the conditions in the eye 2 after a vitreous detachment; the resulting forces on the retina 6, which can lead to a retinal detachment, are depicted schematically. FIG. 4 also shows preferred incision geometries 7 which cause the vitreous humor 5 (or the vitreous humor strands 8) to be cut up, leading to a relief of the retina 6.

Figure 5:
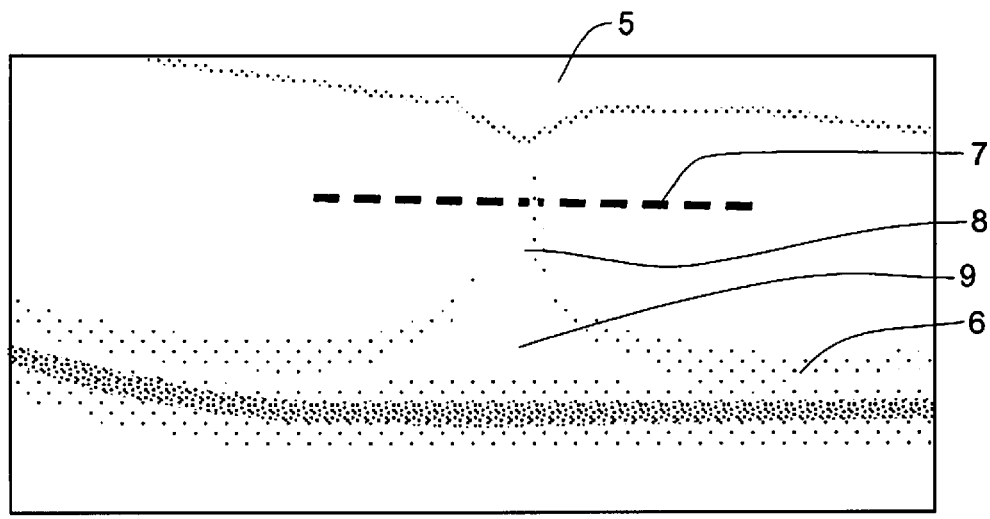
FIG. 5 depicts an OCT image of a retinal detachment.

FIG. 5 shows an OCT cross-sectional image of the retina 6, in which a vitreous humor strand 8 has caused the detachment 9 of the retina 6. By severing the vitreous humor strand 8 along the incision geometry 7, the tension on the retina is decreased and it can, if applicable, return to its original position.

Figure 6:
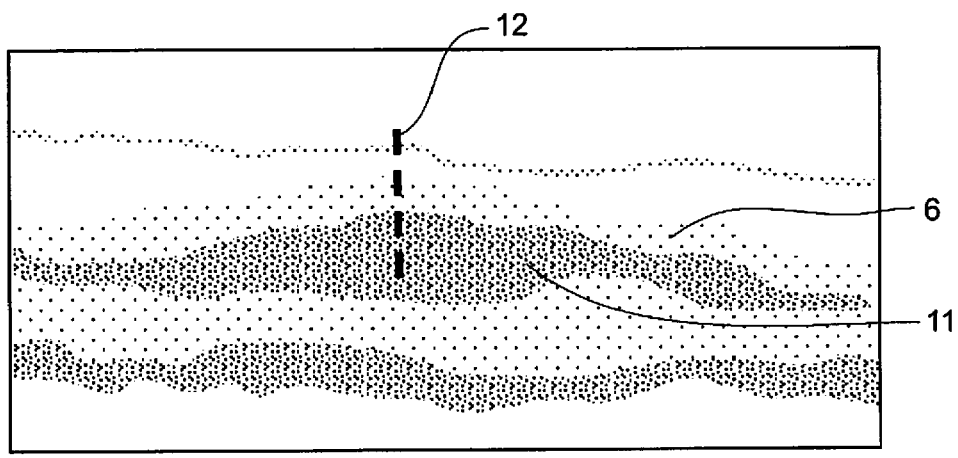
FIG. 6 depicts an OCT image of a cystoid macular edema.

FIG. 6 shows an OCT cross-sectional image of a cystoid macular edema which causes an accumulation 11 of liquid below the retina 6. With the use of the treatment laser, a channel 12 through the retina 6 is generated, through which the liquid can flow into the vitreous humor.

The invention claimed is:

1. A device to produce minimally invasive incisions in a retina, comprising:
   a femtosecond laser source emitting laser radiation;
   a control device in operable communication with the femtosecond laser source programmed to guide placement of incisions in the retina based on navigation, the navigation being based on optical coherence tomography (OCT) imaging produced by a detection device in operable communication with the control device wherein the control device is programmed and the femtosecond laser source is calibrated to execute retinal layer selective laser surgery in the retina;
   wherein the femtosecond laser source emits laser radiation in a green spectral range that is selectively absorbed by a retinal pigment epithelium of the eye and the control device is programmed to provide control data to the laser source and to control a deflection unit to guide a focal point of laser radiation emitted by the femtosecond laser source such that the incisions are selective for the retinal pigment epithelium; and
   a scanner mirror under control of the control device that laterally shifts a focal position of a femtosecond laser beam emitted by the femtosecond laser source and an optical beam guidance system under control of the control device that images the scanner mirror at a conjugate plane to the scanner mirror at a location that can be placed proximate the pupil of an eye to be treated.

2. The device as claimed in claim 1, wherein the OCT imaging and the femtosecond laser source are structured to cut out all or a portion of a macular region of the retina to facilitate macular rotation.

3. The device as claimed in claim 1, wherein the femtosecond laser source emits radiation at a wavelength of 532 nm.

4. The device as claimed in claim 1, further comprising focusing optics for the laser system, the focusing optics having a numerical aperture of 0.05 to 0.2.

5. The device as claimed in claim 4, wherein the focusing optics for the laser system have a numerical aperture of 0.1.

6. The device as claimed in claim 1, further comprising a contact glass that couples the eye to the laser system.

7. A device for vitreous humor surgery using a laser, comprising:
   a laser system including a femtosecond laser and a deflection unit that guides a femtosecond laser beam;
   a detection device that determines geometric variables in an eye posterior segment; and
   an optical beam guidance system configured to have an image plane and a conjugate image plane that are located on opposing sides of the optical beam guidance system, wherein the optical beam guidance system is further configured such that the image plane is located at a scanner mirror of the deflection unit when the conjugate image plane is located at a pupil of the eye that is to be treated during treatment wherein scanning of a focal point of the femtosecond laser beam by the deflection unit over a retina and a vitreous body of the eye to be treated is facilitated;
   wherein the detection device is connected to a control device that is programmed to determine a desired incision geometry for the laser system from geometric variables and programmed to control the laser and the deflection unit correspondingly to execute the desired incision geometry when the conjugate image plane is located at the pupil of the eye that is to be treated.

8. The device according to claim 7, wherein the control device detects the geometric variables three-dimensionally and a control process takes into account the three-dimensionality.

9. The device according to claim 7, further comprising a contact glass that couples the eye to the laser system.

10. The device according to claim 7, further comprising focusing optics for the laser system, the focusing optics having a numerical aperture of about 0.05 to about 0.2.

11. The device according to claim 10, wherein the focusing optics for the laser system have a numerical aperture of about 0.1.

12. The device according to claim 7, wherein the control device takes into account the optical imaging properties of cornea and crystalline lens of the eye during the control process.

13. The device according to claim 7, further comprising a coagulating, continuously emitting laser in a green, yellow, and red spectral range whereby, in addition to a cutting effect of the femtosecond laser, bleeding can be coagulated.

14. The device according to claim 7, wherein the optical beam guidance system laterally shifts the focal position in the conjugate image plane located at the pupil of the eye.

15. The device for vitreous humor surgery using a laser as claimed in claim 7, further wherein the control data provided to the laser source is inclusive of calculating parameters of the laser radiation locally on the retina using an optical model.

* * * * *